United States Patent
Adams et al.

(10) Patent No.: US 11,602,427 B2
(45) Date of Patent: Mar. 14, 2023

(54) INTRAOCULAR LENSES INCLUDING AN INTRAOCULAR PRESSURE SENSOR

(71) Applicant: QURA, INC., Sudbury, MA (US)

(72) Inventors: Douglas P. Adams, Sudbury, MA (US); Jean-Noel Fehr, Neuchatel (CH); Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 0 days.

(21) Appl. No.: 17/040,066

(22) PCT Filed: Apr. 1, 2019

(86) PCT No.: PCT/US2019/025102
§ 371 (c)(1),
(2) Date: Sep. 22, 2020

(87) PCT Pub. No.: WO2019/191748
PCT Pub. Date: Oct. 3, 2019

(65) Prior Publication Data
US 2021/0030529 A1    Feb. 4, 2021

Related U.S. Application Data

(60) Provisional application No. 62/650,855, filed on Mar. 30, 2018.

(51) Int. Cl.
*A61F 2/16* (2006.01)
*A61B 5/00* (2006.01)

(52) U.S. Cl.
CPC .......... *A61F 2/1613* (2013.01); *A61B 5/6821* (2013.01); *A61B 2562/0214* (2013.01);
(Continued)

(58) Field of Classification Search
CPC ............ A61F 2/1613; A61F 2002/1681; A61F 2210/0014; A61F 2250/0002;
(Continued)

(56) References Cited

U.S. PATENT DOCUMENTS 6,443,893 B1 *  9/2002  Schnakenberg ..... A61B 5/0031
                                                  600/398
6,796,942 B1 *  9/2004  Kreiner ................ A61B 5/0031
                                                  600/398
(Continued)

FOREIGN PATENT DOCUMENTS

DE    19858172 A1 *  6/2000  ............... A61B 3/16
EP    2763581 B1    1/2018
(Continued)

OTHER PUBLICATIONS

Farandos et al., "Contact lens sensors in ocular diagnostics." Advanced healthcare materials 4.6 (2015): 792-810.
(Continued)

*Primary Examiner* — Javier G Blanco
(74) *Attorney, Agent, or Firm* — Smith Baluch LLP

(57) ABSTRACT

Intraocular lenses that include a central portion and one or more peripheral portions. The IOLs includes a sensor housing and a communication member, both of which are secured to the central portion.

12 Claims, 4 Drawing Sheets

(52) U.S. Cl.
CPC ............... *A61B 2562/0247* (2013.01); *A61F 2002/1681* (2013.01); *A61F 2210/0014* (2013.01); *A61F 2250/0002* (2013.01)

(58) Field of Classification Search
CPC .......... A61B 5/6821; A61B 2562/0214; A61B 2562/0247; A61B 3/16
See application file for complete search history.

(56) References Cited

U.S. PATENT DOCUMENTS

| | | | |
|---|---|---|---|
| 8,475,374 | B2 | 7/2013 | Irazoqui et al. |
| 9,078,613 | B2 | 7/2015 | Irazoqui et al. |
| 9,173,564 | B2 | 11/2015 | Choo et al. |
| 9,247,877 | B2 * | 2/2016 | Elsheikh ............... A61B 3/16 |
| 9,596,988 | B2 | 3/2017 | Irazoqui et al. |
| 9,662,021 | B2 | 5/2017 | Chow et al. |
| 10,044,227 | B2 | 8/2018 | Chappell et al. |
| 10,426,341 | B2 | 10/2019 | Choo et al. |
| 2010/0137694 | A1 | 6/2010 | Irazoqui et al. |
| 2012/0226133 | A1 * | 9/2012 | Wong .................. A61B 5/6846 600/398 |
| 2012/0238857 | A1 * | 9/2012 | Wong .................. A61F 2/16 600/398 |
| 2014/0371560 | A1 * | 12/2014 | Etzkorn ................. A61B 5/682 600/365 |
| 2016/0374576 | A1 * | 12/2016 | Ziaie .................... A61B 5/205 600/561 |
| 2017/0115511 | A1 | 4/2017 | Beaton et al. |
| 2017/0164831 | A1 | 6/2017 | Choo et al. |
| 2017/0209045 | A1 * | 7/2017 | Choo .................... A61B 3/16 |
| 2018/0035888 | A1 | 2/2018 | Irazoqui et al. |
| 2018/0375382 | A1 | 12/2018 | Chappell et al. |
| 2019/0175015 | A1 | 6/2019 | Adams et al. |
| 2020/0237218 | A1 | 7/2020 | Irazoqui et al. |

FOREIGN PATENT DOCUMENTS

| | | | | |
|---|---|---|---|---|
| WO | WO-2012157623 | A1 * | 11/2012 | ........... A61F 2/1613 |
| WO | WO-2013050073 | A1 * | 4/2013 | ............... A61B 3/16 |
| WO | 2013090886 | A1 | 6/2013 | |
| WO | WO-2016122241 | A1 * | 8/2016 | ............... A61B 5/22 |
| WO | 2017210316 | A1 | 12/2017 | |
| WO | 2019164940 | A1 | 8/2019 | |
| WO | 2019191748 | A1 | 10/2019 | |
| WO | 2019216945 | A1 | 11/2019 | |
| WO | 2020023036 | A1 | 1/2020 | |
| WO | 2020046299 | A1 | 3/2020 | |
| WO | 2020081072 | A1 | 4/2020 | |
| WO | 2020160262 | A1 | 8/2020 | |
| WO | 2020236139 | A1 | 11/2020 | |

OTHER PUBLICATIONS

International Search Report and Written Opinion in International Patent Application No. PCT/US2019/025102 dated Jul. 2, 2019, 15 pages.

Leonardi et al., "Wireless contact lens sensor for intraocular pressure monitoring: assessment on enucleated pig eyes." Acta ophthalmologica 87.4 (2009): 433-437.

* cited by examiner

INTRAOCULAR LENSES INCLUDING AN INTRAOCULAR PRESSURE SENSOR

CROSS REFERENCE TO RELATED APPLICATIONS

This application is a national-stage application of International Application No. PCT/US2019/025102, which was filed on Apr. 1, 2019, and which in turn claims the benefit of U.S. Provisional Application No. 62/650,855, filed Mar. 30, 2018. Each of these applications is incorporated by reference herein in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular lenses ("IOLs") are typically permanent, plastic lenses that are surgically implanted inside of the eyeball to replace or supplement the eye's natural crystalline lens. They have been used in the United States since the late 1960s to restore vision to cataract patients, and more recently are being used in several types of refractive eye surgery.

The natural crystalline lens is critical component of the complex optical system of the eye. The crystalline lens provides about 17 diopters of the total 60 diopters of the refractive power of a healthy human eye. Most intraocular lenses used in cataract surgery may be folded and inserted through the same tiny opening that was used to remove the natural crystalline lens. Once in the eye, the lens may unfold to its full size. The opening in the eye may be as small as 2.5 mm in length, so that it heals itself quickly without stitches. The intraocular lenses may be made of inert materials or they may have a biocompatible coating that does not trigger rejection responses by the body.

In most cases, IOLs are permanent. They rarely need replacement, except in the instances where the measurements of the eye prior to surgery have not accurately determined the required focusing power of the IOL. Also, the surgery itself may change the optical characteristics of the eye. In most cases, the intraocular lenses implanted during cataract surgery are monofocal lenses, and the optical power of the IOL is selected such that the power of the eye is set for distance vision. Therefore, in most cases the patient will still require reading glasses after surgery. Intraocular lens implants may be static multifocal lenses, which attempt to function more like the eye's natural lens by providing clear vision at a distance and reasonable focus for a range of near distances, for patients with presbyopia. Recently, intraocular lenses have been implanted in canines, mainly household pet dogs, after cataract extraction. Commonly affected breeds include the American cocker spaniel, poodle, Boston terrier, miniature Schnauzer, Bichon Frise, and Labrador retriever. Typically, genetic lenticular opacities are bilateral and slowly progressive. Rapidly progressive cataracts commonly occur in dogs with diabetes mellitus. Secondary lens-induced uveitis is a frequent finding that may complicate pre- and postoperative management (Cook, C, "Canine Cataract Surgery", in *Cataract & Refractive Surgery Today*, 2008; pp 32).

An exemplary intraocular lens 10 developed for implantation in canines is shown in FIG. 1, which is a hydrophilic posterior chamber intraocular implant (PCL) developed for canines.

Exemplary dimensions of this intraocular lens and its intended site of implantation are provided in Table 1.

TABLE 1

| | |
|---|---|
| Application | For implantation into the capsular bag |
| Optic size optic body | 6.0 mm (60 V-11) |
| | 6.5 mm (60 V-12) |
| | 6.5 mm (60 V-13) |
| | 6.5 mm (60 V-14) |
| Clear optic | 6.0 mm |
| Overall length | 11.0 mm, 12.0 mm, 13.0 mm, 14.0 mm |
| Haptic angulation | 0° |
| Haptic design | Square-edged haptic and optic |
| Optic design | Biconvex |
| Material | Hydrophilic acrylate with 25% water content and UV-blocker |
| Sterilization method | Autoclaving, exposure to Ethylene oxide, exposure to gamma rays |
| Available diopter | +41.0 D |

A considerable number of patients needing to undergo cataract surgery have preexisting glaucoma. Glaucoma has been diagnosed in nearly 15% of the population in USA above age 80. The incidence of glaucoma rises with age, and is more prevalent in the African American and Hispanic population segment in USA. Many of these patients develop cataract at an earlier age (typically between 50 and 75 years of age), and undergo cataract extraction and in virtually all cases implantation of an intraocular lens. Many of these pseudophakes or aphakes, especially those with diabetes may develop glaucoma, including angle closure glaucoma caused by post-operative inflammation.

Postoperative increase in intraocular pressure may be caused by residual viscoelastic gels left over after surgery, incursion of the vitreous caused by breach of the posterior capsule during cataract surgery, or iatrogenic damage to the iris, leading to pigment dispersion or the Ugh (uveitis-glaucoma-hyphema) syndrome. Moreover a certain percentage of persons who develop glaucoma at a relatively early age subsequently develop cataract and undergo cataract extraction and implantation of an intraocular lens.

Models based on UN world population projections predict that in the year 2020, 79.6 million persons will be afflicted with either open-angle glaucoma (OAG) or angle-closure glaucoma (ACG) with 5.9 million and 5.3 million projected to be bilaterally blind from these two conditions, respectively. (Kung, J S, et al, "Cataract surgery in glaucoma patient" in Middle east Afr J Ophthalmol, 2015; 22(1), pp 10-17.).

Occurrence of glaucoma after cataract surgery is especially prevalent in canines, partly because canines tend to experience a substantially higher level of postoperative inflammation subsequent to cataract surgery.

The prevalence of the primary breed-related glaucomas has gradually increased from 0.29% (1964-1973); 0.46% (1974-1983); 0.76% (1984-1993); to 0.89% (1994-2002). Breeds that consistently featured among the highest 10 for glaucoma prevalence from four different periods (1964 to 2002) included American Cocker Spaniel, Basset Hound, Wire Fox Terrier, and Boston Terrier. During the last observation period (1994-2002), 22 different breeds had 1% or higher prevalence of the glaucomas. The highest prevalence of glaucomas in 1994-2002 by breed included: American Cocker Spaniel (5.52%); Basset Hound (5.44%); Chow Chow (4.70%); Shar-Pei (4.40%); Boston Terrier (2.88%); Wire Fox Terrier (2.28%); Norwegian Elkhound (1.98%); Siberian Husky (1.88%); Cairn Terrier (1.82%); and Miniature Poodle (1.68%). A predominance of females with glaucoma occurred in the American Cocker Spaniel, Basset Hound, Cairn Terrier, Chow Chow, English Cocker Spaniel, Samoyed, and perhaps the Siberian Husky, and a predominance of males in the Australian Cattle dog and St Bernard. Age affected the time for first presentation of the glaucoma in the pure-bred dog. In the majority of breeds the glaucoma was presented for initial diagnosis in dogs between 4 and 10 years of age, as reported in Gellat K N, and McKay, EO, "Prevalence of the breed related glaucoma in pure bred dogs in North America", in *Vet Ophthalmol,* 2004; 7(2), pp 97).

Biros, et al, reported a study of 346 canine eyes, in which they monitored incidence of glaucoma as a function of eight variables, including breed, sex, post-operative hypertension, and intraocular lens placement. Of the 346 eyes, 58 (16.8%) developed glaucoma after surgery. At 6 months, 32 of 206 (15.5%) eyes examined had glaucoma; at 12 months, 44 of 153 (28.8%) eyes examined had glaucoma. Median follow-up time was 5.8 months (range, 0.1 to 48 months). Mixed-breed dogs were at a significantly lower risk for glaucoma, compared with other breeds. Eyes without IOL placement were at a significantly lower risk for glaucoma, compared with eyes with IOL placement. Eyes with hypermature cataracts were at a significantly higher risk for glaucoma, compared with eyes with mature or immature cataracts, as reported in Biros, et al, "Development of glaucoma after cataract surgery in dogs", in *J. Am Vet Med Assoc.,* 2000; 216(11), pp 1780).

Therefore, regular and frequent monitoring of intraocular pressure is critically important during the immediate post-operative period, following cataract surgery. In the long run, regular monitoring of intraocular pressure is required to track continued efficacy of pressure controlling medications and monitor compliance. Both of these needs require introduction of an implanted, intraocular pressure sensor that can wirelessly transmit data to an external unit without any involvement of the patient.

SUMMARY OF THE DISCLOSURE

One aspect of this disclosure is an intraocular lens ("IOL"), comprising: a central portion that includes an optic; a housing that includes an intraocular pressure ("IOP") sensor; an annular antenna in communication with the housing, wherein the housing and antenna are secured to the central portion, and wherein the annular antenna is disposed around a periphery of the central portion; and a peripheral haptic portion disposed radially outside of the central portion.

The housing may be mounted to an anterior surface of the central portion. The annular antenna may be mounted to the anterior surface of the central portion.

The annular antenna may form a complete loop.

The central portion may have a circular configuration.

The housing may be a hermetically sealed package.

The housing may further comprise an electronic module.

The IOP sensor may comprise a capacitive sensor.

The IOP sensor may comprise a piezoresistive sensor.

The IOP sensor may have dimensions of about 0.5 mm×0.7 mm×1.0 mm.

The annular antenna may comprise at least one of titanium and nitinol coated with Gold.

The annular antenna may have a diameter from 7.0 mm to 5.0 mm.

The annular antenna may have a thickness of 25 microns to 100 microns.

The annular antenna can have a partial loop configuration.

A portion of the sensor housing may be secured to the peripheral portion.

The sensor housing may not extend beyond an anterior surface profile on the optic.

The sensor housing may be disposed in a cavity formed in the optic. The cavity may have a depth of 0.1 mm to 0.6 mm.

The sensor housing may be encased in a sealed pouch. The sealed pouch may be made of a barrier film, such as polyvinylidene difluoride or Paralyene. The sealed pouch may be filled with an inert incompressible fluid, such as a low molecular weight silicone oil. The sealed pouch or cavity may be 300 microns×500 microns×500 microns.

The sensor housing may be radially aligned with the optic such that a long axis of the sensor housing passes through an optical axis of the optic.

The IOP sensor may be radially closer to an optic optical axis than the antenna.

The IOP sensor may be radially closer to an optical axis than an electronics module of the sensor housing.

The antenna may be in electrical communication with an electronics module of the sensor housing.

The sensor housing may be disposed in the optic, but does not extend to an optical axis of the optic.

A portion of the antenna may be embedded in the central region, and a portion may extend above the central region to form a raised annular antenna region.

One aspect of the disclosure is a method of manufacturing any of the IOLs herein.

DETAILED DESCRIPTION

The present disclosure is related to the field of Intraocular Lenses ("IOLs"). The IOLs generally include a central portion that includes an optic, and a peripheral portion disposed and extending radially from the central portion. In particular, the present disclosure relates to IOLs wherein a sensor housing is attached (directly or indirectly) to the central region of the IOL in such a way that the sensor housing does not significantly affect the optical performance or stability of the IOL in the eye. Preferably, the sensor is an intraocular pressure ("IOP") sensor. The IOLs herein can be implanted into a posterior chamber of an eye, such as within a capsular bag from which a native crystalline lens has been removed.

One aspect of the disclosure is an implantable device (e.g., an IOL) that includes a central portion that includes an optic and a peripheral portion disposed radially outside the central portion. The implantable device also includes a sensor housing that includes an intraocular pressure ("IOP") sensor, and an annular antenna in communication with the housing, wherein the antenna and at least a portion of the sensor housing are secured to the central portion, and wherein the annular antenna is disposed around a periphery of the central portion.

Figure 1:
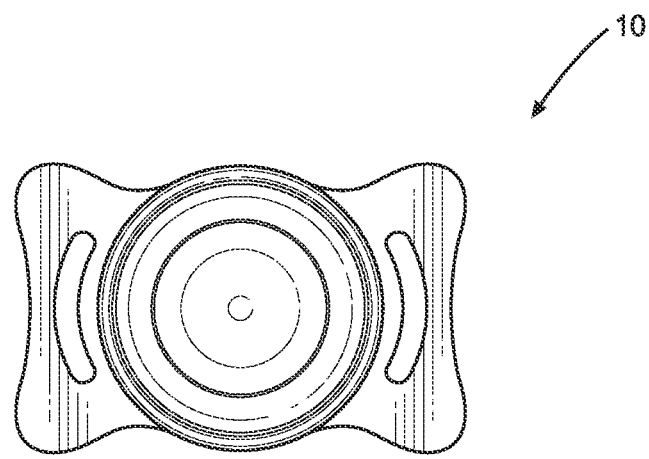
FIG. 1 is an exemplary IOL without a sensor housing.

FIG. 1 illustrates an exemplary IOL that includes a sensor housing and an antenna. IOL 20 includes central region 22 and peripheral regions 24. The peripheral regions 24 each include two haptics 25, which are configured to secure the IOL within the eye, such as within a capsular bag from which the native IOL has been removed. Central region 22 includes an optic 26, which can be configured in any way desired. The IOL 20 includes a region in which the central region 22 transitions to the peripheral region(s) 24. Central region 22 and peripheral regions 24 may be integrally formed, forming a one piece intraocular lens (e.g., formed of the same polymeric material in a mold) rather than being two different components secured together. The central region 22 can also include a peripheral central region that is radially outside of the optic portion 26 and serves as the transition between the central region 22 and the peripheral region 24. Alternatively, the entirety of the central region 22 can be made up of optic 26, with the peripheral regions 24 extending directly from the optic 26.

IOL 20 also includes communication member 28, which in this embodiment is a circularly configured antenna. A circular antenna may form a complete loop, or it can have a partial loop configuration. IOL 20 also includes sensor housing 21, which houses therein or thereon at least one type of sensor, such as an intraocular pressure sensor that is adapted to sense or used in the detecting of intraocular pressure. The IOL can thus serve as both an intraocular lens, as well as facilitate the sensing or detecting of intraocular pressure. Sensor housing 21 may be a hermetically sealed housing, with the sensor disposed such that it can detect changes in intraocular pressure in the environment ambient to the sensor housing. The sensor housings and antennas herein may be directly or indirectly mounted to the IOL.

Figure 2:
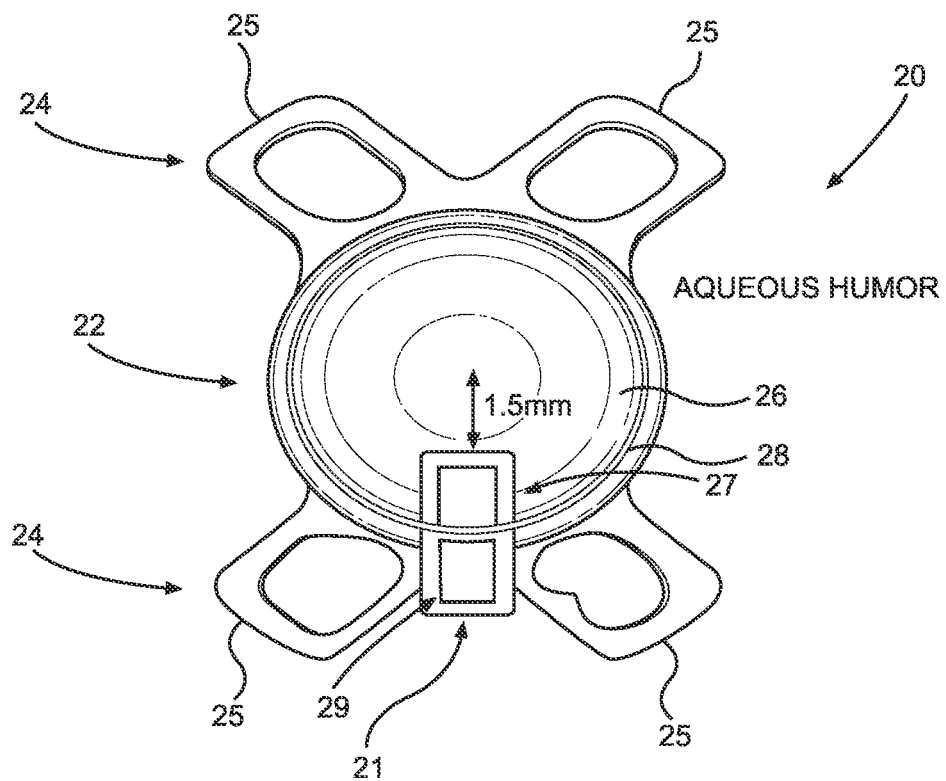
FIG. 2 is an exemplary IOL with a sensor housing.

The communication members herein (e.g., antenna 28) may be disposed around and mounted to a periphery of the central portion, as is shown in FIG. 2. The sensor housing and the antenna may be mounted to an anterior surface of the central portion, as shown in FIG. 2. The annular antenna may form a complete loop, as shown in FIG. 2. The central portion of the IOL may have a circular configuration, as shown in FIG. 2. As shown in FIG. 2, a portion 29 of the sensor housing is secured to the peripheral portion, although in some alternatives to FIG. 2 only the portion of the sensor housing that is disposed over the central region is attached to the IOL, and the remainder of the sensor housing may float over (without being directly attached) to the peripheral portion.

In any of the embodiments herein, the antenna can be a coil or wire, and can be made of, for example without limitation, a gold-titanium alloy, and/or can be coated with gold. In some embodiments the loop antenna can form a loop with a diameter of 5.0 mm to 7.0 mm, such as in the range of 5.5 mm to 6.5 mm. The antenna may have a diameter in the range from 25 microns to 200 microns, such as 50-150 microns, such as 100 microns.

The communication component (e.g., antenna) is coupled to and in communication with the sensor housing. Sensor housing 21 includes IOP sensor or IOP sensor module 27. The antenna is preferably mounted on an anterior surface or side of the IOL, but it may be mounted to a posterior surface. The IOL may have formed therein a circular crevice or depression, and the antenna can be seated in the circular crevice or depression. The crevice or depression may be formed in a coating on the intraocular lens. The overall thickness of the coating may be, for example without limitation, about 90-110 microns, such as 100 microns. The depression formed in a coating may be 25-75 microns deep, and a portion of the antenna, when seated in the depression, may extend above the depression and form a raised barrier around the circumference of the central portion of the intraocular lens. The antenna may be further coated with a coating of thickness 50-150 microns, preferably about 100 microns. Since the edge of the central portion has a thickness in the range of 50-150 microns, the overall thickness of the edge bearing the antenna will be in the range of 150-525 microns, preferably 200-400 microns. This increase in edge thickness and a barrier on the anterior surface may eliminate migration of residual cortical and equatorial cells left over after phacoemulsification and cleaning of the capsular sac prior to lens implantation to the posterior capsule, and thus helps inhibit posterior capsular opacification ("PCO").

Figure 3B:
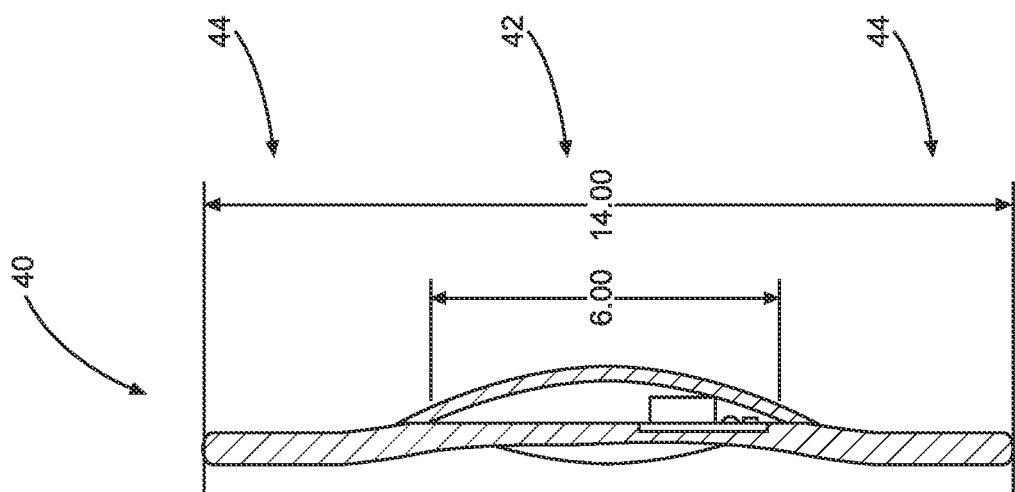
FIGS. 3A and 3B illustrate an exemplary IOL with a sensor housing.
Figure 3A:
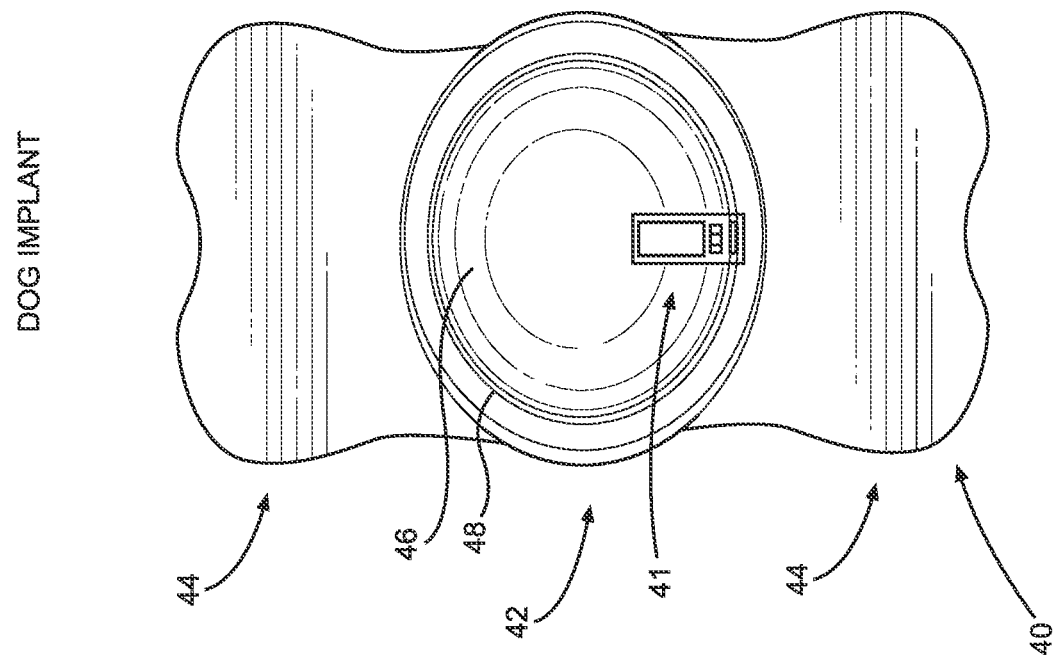

FIGS. 3A and 3B illustrate top and side views, respectively, of an exemplary canine posterior chamber IOL 40 with an intraocular pressure sensor housing 41 and antenna 48 positioned on the anterior surface of the IOL. IOL 40 is very similar to IOL 20 from FIG. 2, but peripheral portions 44 that extend from central portion 42 have more of a plate configuration than those in FIG. 2. The sensor housing 41 also extends less into the peripheral portion 44 than does sensor housing 21 from FIG. 2. That is, sensor housing 48 extends over central region 42 and not over the peripheral region(s) 44. All other descriptions of IOL 20 from FIG. 2 may be incorporated into IOL 40 in FIGS. 3A and 3B.

Figure 4A:
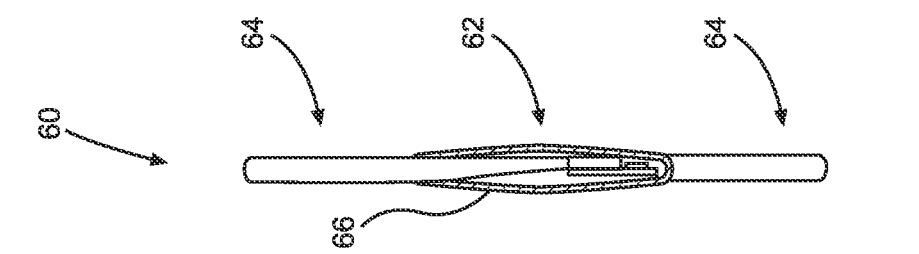
FIGS. 4A and 4B illustrate an exemplary IOL with a sensor housing.
Figure 4B:
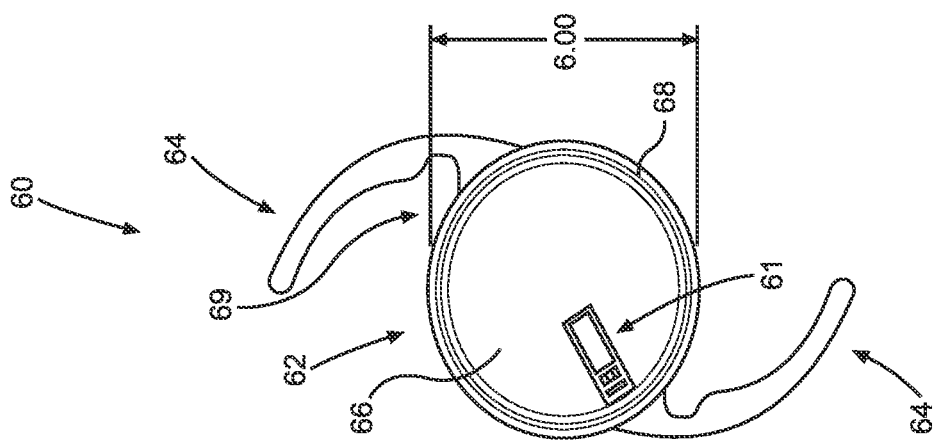

FIGS. 4A and 4B illustrates an exemplary IOL 50 that is designed for human use. IOL 50 can be similar to other IOLs herein and can incorporate other features even if not expressly incorporated into this embodiment. IOL 50 includes central region 52 and peripheral regions 54 extending from central region 52. Peripheral regions 54 in this embodiment are each a haptic with a wire configuration, which are generally known in the art. IOL 50 includes sensing housing 51 and antenna 58 mounted to central region 52. Sensor housing 51 includes a sensor such as a IOP sensor. IOL 50 includes optic 56. FIG. 4B illustrates an exemplary dimension for the IOL.

Figure 5A:
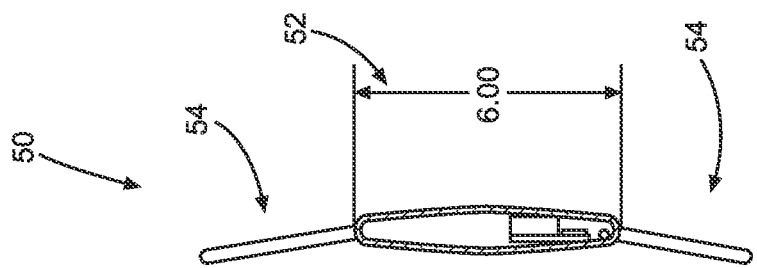
FIGS. 5A and 5B illustrate an exemplary IOL with a sensor housing.
Figure 5B:
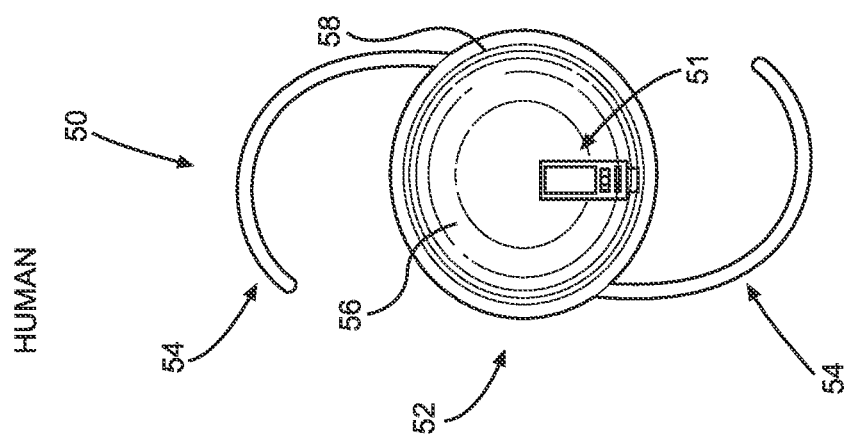

FIGS. 5A and 5B illustrate an exemplary IOL 60 that is very similar to IOL 50 from FIGS. 4A and 4B, and is also designed for human use. IOL 60 can be similar to other IOLs herein and can incorporate other features even if not expressly incorporated into this embodiment. All similarly labeled features from IOL 50 are expressly incorporated by reference in IOL 60 (e.g., optic 51 and 61). In IOL 60, the haptics include hinges 69 that increase a region of increased flexibility, which can help the haptics deform (e.g., for delivery). FIG. 5A illustrates an exemplary dimension for the IOL.

Some embodiments herein include a sensor housing mounted on or to an anterior surface of the IOL. Once the IOL is implanted, portions of the anterior surface of the IOL, particularly where the sensor housing is mounted, may come into contact with the iris. An important design consideration is attempting to reduce the likelihood of, or preferably eliminate, the possibility of the sensor housing chafing the iris. One approach to reducing the likelihood that the sensor housing will cause iris chafing is to have the profile of the sensor not extend beyond the optical surface of the optic portion of the IOL. This is generally shown in the side views of FIGS. 3B, 4B, 5B, wherein the sensor housings do not extend beyond the anterior surface of the optic portion.

One method of manufacturing IOLs such that the sensor housing does not extend beyond an outer profile of the IOL (e.g., does not extend beyond the anterior surface of the optic) is to create a cavity or depression of sufficient depth and configuration in the anterior surface of the central portion of the intraocular lens, and position the sensor housing within the cavity. The depth of this cavity relative to the anterior surface can be about 0.1 mm to 0.6 mm, preferably 0.2 mm to 0.4 mm. The sensor housing is preferably encased in a sealed pouch made of a barrier film, such as polyvinylidene difluoride or Paralyene. The pouch or cavity in which the sensor housing is disposed can be filled with an inert incompressible fluid of low viscosity, such as a low molecular weight silicone oil. The size of the pouch or cavity may be, for example without limitation, 300 microns× 500 microns×500 microns, and it is preferably coated with a biocompatible, non-toxic coating that elicits a muted or minimal post-operative inflammatory response.

After an IOL is implanted in a capsular bag, the capsular bag, including the anterior portion thereof, tends to collapse around the implanted IOL. A pressure sensor, if included in the sensor housing, must not, therefore, be covered by the capsular bag as it collapses around the IOL. The sensing housing, and in particular the pressure sensor, should be disposed in the IOL such that the pressure sensor will not be covered by the anterior capsular bag after the IOL is implanted. Exemplary constructions of the sensor housing and the orientation relative to the optic that can reduce the likelihood of the sensor being covered are shown in FIGS. 3A, 4A and 5A. As shown, the sensor housing is disposed in the IOL such that the sensor module is closest to the center of the optic (i.e., closest to the optical axis). By positioning the sensor housing such that the sensor is disposed away from a periphery of the optic, the likelihood that the sensor will be covered by the capsular bag is reduced. In the exemplary embodiments of FIGS. 3A, 4A, and 5A, the sensor housing has a long axis, which is aligned radially relative to the optic. Stated alternatively, the long axis of the sensor housing passes generally through the optical axis.

In any of the IOLs herein, the antenna can be a loop antenna, shaped to conform to the edge of the central region of the IOL (which includes the optic), and can be made of a biocompatible metal that has a relatively high electrical conductivity, such as Titanium coated with Gold or Nitinol coated with Gold. The thickness of the antenna (e.g., diameter of a wire) may be in the range of 25-150 microns, preferably 50-100 microns. The antenna may be coated with a biocompatible coating.

Any of the IOLs herein may be a single piece IOL or a multipiece IOL. The IOLs may be made of a hydrophobic or a hydrophilic material. Preferably, they are designed to be implanted in the capsular sac, although it may be designed for implantation in the ciliary sulcus or the anterior chamber. The overall diameter of the IOLs may be in the range of 11.0 mm-14.0 mm, preferably in the range 12.0 mm to 14.0 mm. The intraocular lenses are configured to be implanted in a delivery folded configuration, using an insertion device designed for this purpose. IOL inserters are known in the art. The folded configuration of the IOL can resemble a taco or U-Shape, since it is important to minimize folding lines on the antenna. The IOLs can be folded along any axis to create the U-shaped delivery configuration.

Exemplary biocompatible coatings have been disclosed previously. The IOLs herein can be coated with a biocompatible coating. Preferably, the coating is made of a hydrogel material, and comprises two or more layers. The inner layer of the coating may be infused with pharmaceuticals, including an anticlotting agent, an antifibrotic agent, a corticosteroid and some other medicaments that downregulates expression of inflammation mediators such as cytokines. The multilayer coating, similar in molecular structure to an extracellular matrix, prevents adhesion of giant cells, or polymorphic macrophage.

Figure 6:
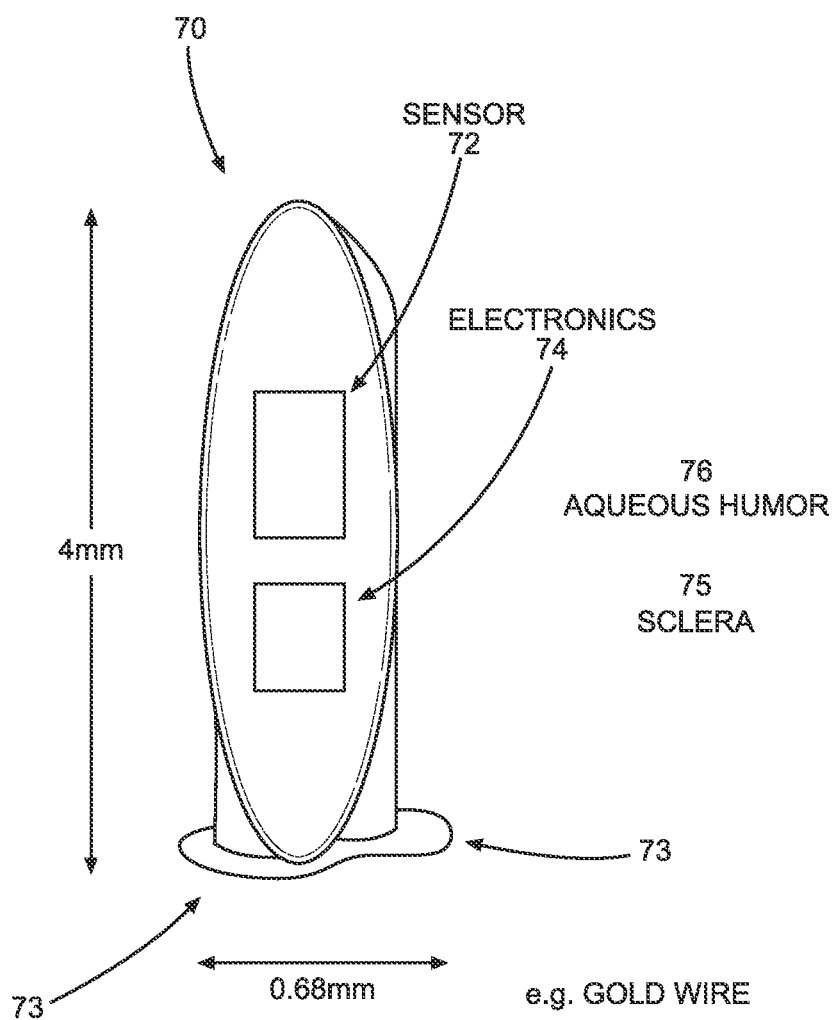
FIG. 6 is an exemplary sensor housing that is not coupled to an IOL.

One aspect of this disclosure is an IOP sensor that acts more as a stand-alone assembly, and is not coupled to an IOL, unlike embodiments above. FIG. 6 illustrates such an exemplary stand-alone IOP FIG. 6 illustrates conceptually an exemplary stand-alone intraocular pressure sensor housing 70, including exemplary dimensions. The generally oval shaped line 78 depicts an antenna. Sensor housing 70 capable of being implanted ab-interno during cataract surgery, with its fixation point, comprising fins 73 (three shown) at the distal end mounted on the sclera, and its proximal end comprising the sensor 72 positioned in the iridocorneal angle. Sensor housing 70 also includes electronics module 74, which are in electrical communication with antenna 78.

The invention claimed is:

1. An intraocular lens ("IOL"), comprising:
a central portion that includes an optic;
a sensor housing that includes an intraocular pressure ("IOP") sensor and an electronic module;
an annular antenna in communication with the sensor housing, wherein the sensor housing and antenna are secured to the central portion, and wherein the annular antenna is disposed around a periphery of the central portion; and
a peripheral haptic portion disposed radially outside of the central portion,
wherein the sensor housing is disposed in the optic and is radially aligned with the optic such that a long axis of the sensor housing passes through an optical axis of the optic,
wherein the sensor housing is encased in a sealed pouch, wherein the sealed pouch is made of a barrier film, and wherein the barrier film comprises at least one of polyvinylidene difluoride or Parylene.

2. The IOL of claim 1, wherein the sensor housing is mounted to an anterior surface of the optic.

3. The IOL of claim 2, wherein the annular antenna is mounted to the anterior surface of the central portion.

4. The IOL of claim 1, wherein the sensor housing is a hermetically sealed package.

5. The IOL of claim 1, wherein the IOP sensor comprises at least one of a capacitive sensor or a piezoresistive sensor.

6. The IOL of claim 1, wherein the annular antenna comprises at least one of titanium and nitinol coated with gold.

7. The IOL of claim 1, wherein the annular antenna has a diameter from 5.0 mm to 7.0 mm.

8. The IOL of claim 1, wherein the annular antenna has a thickness of 25 microns to 100 microns.

9. The IOL of claim 1, wherein a portion of the sensor housing is secured to the peripheral haptic portion.

10. The IOL of claim 1, wherein the sensor housing is disposed in a cavity formed in the optic.

11. The IOL of claim 10, wherein the cavity has a depth of 0.1 mm to 0.6 mm.

12. The IOL of claim 1, wherein the sealed pouch is filled with an inert incompressible fluid.

* * * * *